United States Patent [19]

Blasius, Jr. et al.

[11] Patent Number: 4,718,889
[45] Date of Patent: Jan. 12, 1988

[54] APPLICATOR SWAB

[75] Inventors: William G. Blasius, Jr., Higganum; Joseph F. Zygmont, Jr., Clinton, both of Conn.

[73] Assignee: Chesebrough-Pond's Inc., Greenwich, Conn.

[21] Appl. No.: 855,668

[22] Filed: Apr. 25, 1986

[51] Int. Cl.⁴ ............................................. A61F 13/00
[52] U.S. Cl. ........................................................ 604/1
[58] Field of Search ............ 15/244 R, 244 C, 209 R; 132/88.7; 604/2, 1; 128/269

[56] References Cited

U.S. PATENT DOCUMENTS 2,006,539 7/1935 Deford ............................. 15/210 R
2,490,168 12/1949 Strauss ................................... 604/2
3,591,885 7/1971 Fritzen ............................. 15/210 R Primary Examiner—Robert Peshock
Attorney, Agent, or Firm—Melvin H. Kurtz; Richard P. Fennelly

[57] ABSTRACT

The present invention is an improved applicator swab which contains a resilient cushion element between the end of the applicator stick and the adherent, absorbent swab tip for the applicator swab. The presence of the cushion element, which is preferably formed of a soft, resilient hot melt adhesive, gives an added degree of protection should the end of the stick holding the swab tip protrude through the body of the tip upon being manipulated by the end user of the applicator swab.

12 Claims, 2 Drawing Figures

APPLICATOR SWAB

BACKGROUND OF THE PRESENT INVENTION

1. Field of the Invention

The present invention relates to an improved applicator swab which can be used, for example, in cleaning the outer human ear and nasal passages, and which can also be used for cosmetic purposes and the like.

2. Description of the Prior Art

Applicator swabs formed by placing a swab tip comprising an absorbent material (e.g., cotton) on an applicator stick (e.g., of wood, paper, plastic, or the like) are well known. In order to properly mount the swab tip on the stick, a number of prior art patents have generally disclosed placing a thin adhesive coating on the stick at the point at which the swab tip is to be placed. Examples of patents which carry such a disclosure include the following: U.S. Pat. Nos. 2,705,009; 3,179,108; 3,255,494; 3,443,562; 3,586,380; and 4,259,955. The prior art utilized such adhesive coatings in thicknesses that did not measurably alter the cross-sectional area of that portion of the stick to which the adhesive was affixed (e.g., see Col. 2, lines 24–29 of U.S. Pat. No. 3,443,562).

In prior art swab constructions (which are intended for use in the outer ear as contrasted to the inner ear canal), it is possible, through improper use by the user, to deform the configuration of the swab tip, for example, when placed in the outer human ear, such that the relatively rigid end of the stick can protrude through the softer swab tip body. Protrusion of the stick through the swab tip is undesirable since such protrusion can cause discomfort and possible physical damage to the person utilizing the swab. U.S. Pat. No. 3,871,375 to R. A. Bennett solves the potential problem of presenting a sharp-ended stick to a person's body by a distinctly different manner than taught for the present invention. Bennett proposes a one-piece, unitary molded swab in which a low porosity, slightly more rigid, shaft portion merges gradually with a high porosity, softly resilient, tip portion which can be presented to the user's body.

SUMMARY OF THE PRESENT INVENTION

The present invention is an improved applicator swab which includes a cushion element mounted over at least one end of the applicator stick between the stick and the adherent, absorbent swab tip. The presence of the cushion element, which is preferably formed of a soft polymeric material (e.g., a polymeric material also having adhesive properties), provides the end of the stick with a softer, more protective site should the swab tip be deformed to such an extent that the end of the stick protrudes through the body of the swab tip.

DESCRIPTION OF THE DRAWINGS

The present invention is further illustrated by the following Drawings which illustrate certain embodiments of the present invention and which form a portion of the present specification, wherein.

DETAILED DESCRIPTION OF THE PRESENT INVENTION

Figure 1:
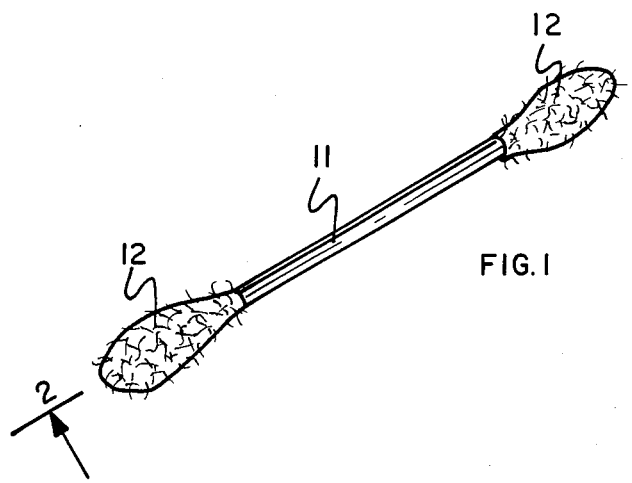
FIG. 1 is a view in perspective of a preferred embodiment of the present invention which includes two swab tips mounted at opposite sides of a stick.
Figure 2:
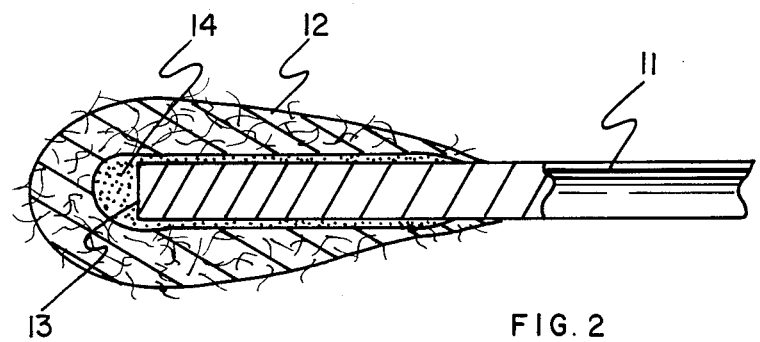
FIG. 2 is a sectional view taken in the direction of the arrows shown in FIG. 1 which illustrates the cushion element embodiment of the present invention in greater detail.

As illustrated in FIG. 1 in the Drawings, a preferred embodiment of the present invention comprises an applicator stick 11 carrying two absorbent swab tips 12 at either end of the applicator stick. As shown in greater detail in FIG. 2, the end 13 of applicator stick 11 has mounted thereon a cushion element 14 which is preferably formed of a soft, resilient adhesive material. The cushion element which can be used in regard to the present invention should have certain properties. It needs to have good adhesion to the material forming the applicator stick 11 (e.g., paper, wood, and/or plastic) as well as the material forming the swab 12 (e.g., any natural or synthetic fiber or blend such as cotton, rayon, and the like) for the most desirable results. Good tensile strength and good resilience, as manifested by resistance to compression set, are desirable. It should most preferably be relatively soft (e.g., a Shore A hardness of from about 5 to 70, preferably from about 10 to about 40). If used on high speed cotton swab assembly machinery, the composition should have a very fast cure time (e.g., from about 0.5 to about 5 seconds). Preferably, the cushion element should be formed of FDA-approved materials if the end product is intended for use in the United States.

Some elastomeric materials which can be used include:

1. Acrylic rubber latex compositions. These materials are generally supplied as a colloidal dispersion (e.g. 30–40% solids) in water. When dried, the reactive sites on the acrylic molecule crosslink yielding a clear rubbery solid with a Shore A hardness of about 50. Preferably, a compatible thickener is added if used in high speed manufacturing to increase the viscosity and a coating wheel would deliver an amount necessary to provide the desired cushion element. Acrylic rubber latex compositions sold under the trademarks RHOPLEX by Rohm and Haas, UCAR by Union Carbide, and HYCAR by B. F. Goodrich are examples of commercially available materials which can be utilized.

2. Urethane rubber latex compositions. These materials function in a similar manner to those described above giving improved tensile strength at the expense of a reduced rebound if the final product is dropped on a hard surface. An example of a suitable commercial product of this type is WITCOBOND from Witco Chemical.

3. Natural rubber latex. This type of material is generally supplied as a 50–60% solids dispersion in water. When dried, the material is slightly amber in color and very resilient. When these are used, it is preferable to use coating wheels to deliver the composition to the stick designed to hold the swab. A second station would then spray a solution of coagulation agent (e.g., calcium chloride, calcium nitrate, aluminum sulfate, or the like) to coagulate the rubber. Later, a third station would repeat coating of the rubber latex composition over the resulting composition to provide a suitable tacky or adhesive surface. Cotton would be applied to this fresh adhesive layer. A commerically available natural rubber latex is HARTEX brand from Firestone.

4. Polyvinyl chloride plastisol. This is a dispersion of PVC in a suitable plasticizer composition. The plastisol can be fused by the application of heat. The final properties of the fused composition include good shock absorption, optical translucence, and a Shore A hardness of 40-70. The plastisol can be applied to the stick by means of coating wheels. A second station would consist of a heat generation source to fuse the plastisol. A final station would apply an adhesive tie layer for later applying of the cotton material. Suitable PVC plastisols are available under the trademark GEON from B. F. Goodrich.

5. Cast urethane. MDI and TDI based monomers, when reacted with anhydrous polyols, form a relatively tough resilient cushion having a Shore A hardness of 50-90. To process this type of material, the isocyanate side of the reaction is blended with polyol and catalyst in a reaction injection molding (RIM) pot. The mixed components can then be metered onto the swab stick and cotton applied immediately thereafter. A suitable commercial product is available under the trademark VIBRATHANE from Uniroyal.

6. Urethane foam. A suitable isocyanate material is commercially available under the trademark HYPOL from W. R. Grace and TREPOL from Twin Rivers Engineering. Highly reactive isocyanates, when combined with water, generate $CO_2$ producing voids which mimic natural sponges. The urethane foam is extremely soft, yet it maintains the tenacity inherent in cured isocyanates. Two methods of production are possible. The first involves a manufacturing process similar to that used to form cast urethanes with the substitution of water for polyol. The second method involves coating of the prepolymer onto the swab stick. Cotton is then directly applied and water utilized during the tip forming process reacts with the prepolymer to yield foam.

7. Thermoplastic elastomers. These materials have the same range of properties as cured thermoset rubber and have the advantage of being melt processable. Their Shore A hardness ranges from about 70-90. They can be applied to the swab stick as a thin tape and wound around the end or ends of the stick. A heating station both seals the tape and makes the surface tacky enough to bond the cotton. A suitable commercially available material of this type is sold under the trademark SANTOPRENE by Monsanto.

8. Room temperature vulcanizing silicones. These semi-transparent rubbers exhibit fair resilience, excellent chemical resistance, and good adhesive properties. The Shore A hardness ranges from 30-60. In order to produce a cushion element tip the composition can be pumped from a dry environment and onto coating wheels. Cotton is then applied immediately thereafter onto the silicone-coated stick. Once exposed to air, the tip will be fully cured in twenty-four hours. A suitable silicone composition is available from General Electric under the designation "RTV".

9. Ethylene-vinyl acetate elastomers. These are commercially available under the trademark ELVAX from DuPont. These thermoplastic elastomers have a broad range of properties depending upon the vinyl acetate concentration and the molecular weight. In general, they are transparent, have good resilience and fair resistance to compression set. Unaltered ethylene-vinyl acetate has a very high melt viscosity and shows a "stringy" rheology which can cause problems in high speed manufacturing operations by undesirably contaminating fresh sticks with stringy adhesive. It is possible to incorporate suitable plasticizers to reduce the viscosity and melt temperature, suitable tackifiers to reduce stringing, and suitable antioxidants to increase pot life. As thus formulated, the material can be applied to the swab stick by coating wheels from a heated glue pot. Until this cushion fully crystallizes, it is quite tacky and cotton can be applied at virtually any time.

A suitable adhesive material which can be used is a hot melt adhesive material such as illustrated in the Examples contained in the present specification.

The construction of the present invention allows for use of the applicator swab with a greater degree of safety. The cushion element 14 forms a protective cap or coating over the applicator stick end should the stick protrude through the swab 12 due to improper manipulation of the swab applicator by the user. As will be understood by persons of ordinary skill in the art, the cushion element embodiment shown herein is broadly useful with all conventional applicator swab products which comprise an applicator stick 11 and swab tip 12.

The following Examples illustrate certain formulations which can be used to make suitable hot melt adhesives that, in a preferred embodiment, can form the cushion element along with certain of the characteristics of such adhesive formulations when applied underneath the swab tips in suitable swab applicators.

EXAMPLES 1-3

The following formulations were made (all amounts are given in parts by weight):

|  | 1 | 2 | 3 |
|---|---|---|---|
| Ethylene/Vinyl Acetate Polymer | 60 | 60 | 100 |
| Polymerized Hydrogenated Rosin Ester | 17.0 | 17.0 | — |
| Dibutyl Phthalate | 23.0 | 11.5 | — |
| Epoxidized Soya Oil | 5.0 | 11.5 | 33.3 |
| Butylated Hydroxytoluene | 0.6 | 0.6 | — |
| CAB-O-SIL Silica | 0.1 | — | — |
| Butyl Benzyl Phthalate | — | — | 50.0 |
| Alicyclic Hydrocarbon Resin | — | — | 83.3 |

The following set forth the viscosity of the adhesive solution, the hardness of the cured element, the resiliency of the cushion element, and the non-stringing characteristics of the element.

|  | 1 | 2 | 3 |
|---|---|---|---|
| Brookfield Viscosity (cps) (LTV #4, 12 RPM, 200° C.) | 25,000 | 33,000 | — |
| Shore "A" Hardness | 20 | 20 | 8 |

The resiliency of the stick end covered with cured adhesive was tested by bouncing the end off a countertop. The element did not stick to the counter and was not deformed by its contact with the counter.

The non-stringing character of the adhesvie was demonstrated by placing a mass of the molten adhesive on a flat spatula followed by rolling the applicator stick end through the adhesive to place a globule of adhesive on the end. The stick with adherent adhesive globule was quickly removed without strings of adhesive forming between the adhesive mass and the removed stick. This non-stringing characteristic is very important in embodiments where the adhesive is applied at high rates of speed from coating wheels to a large plurality of sticks in a commercial speed operation. The lack of adhesive stringing avoids adhesive fouling of the fabrication equipment.

EXAMPLES 4–5

Multiple dips of the end of the swab stick into two differing acrylic rubber latex were required to put about 40 mg. of latex rubber on each stick end making it suitable for the later step of adding a cotton swab tip.

EXAMPLE 6

The swab stick was dipped into a natural rubber latex available under the trademark HARTEX H-103 from Firestone. Before the thus formed rubber bead dripped, it was placed into a saturated solution of calcium chloride in ethyl alcohol. Forth nine milligrams of rubber was applied to the stick end in this manner making it suitable for later application of a cotton swab tip.

EXAMPLE 7

A polyvinyl plastisol was compounded from the following ingredients:

| Ingredient | Amount (Parts by Weight) |
| --- | --- |
| PVC Resin (GEON 138 brand) | 100 |
| Butyl benzyl phthalate (SANTICIZER 160 brand) | 63 |
| Dioctyl phthalate | 27 |
| Epoxidized soya oil (PLASTOFLEX 2307) | 5 |

Paper sticks were dipped into the plastisol and placed in a 210° F. oven for three minutes. The gelled plastisol had a Shore A hardness of 62. The stick was ready for application of a cotton swab tip.

EXAMPLE 8

A urethan foam cushion element was formed on a swab stick using the following formulation: 100 parts by weight of hydrophilic polyisocyanate (TREPOL brand); 150 parts of water; and 2 parts of surfactant (SILICONE L-520). A soft, springy foam was formed on the end of the swab stick making it suitable for the later step of addition of a cotton swab tip.

EXAMPLE 9

A thermoplastic film of urethane (Q-THANE brand from K. J. Quinn) was wrapped around the end of a stick and was treated in a microwave oven for four minutes to soften the urethane element. Cotton was applied as a swab tip after the urethane had been softened.

EXAMPLE 10

The following ethylene-vinyl acetate composition was used to form the cushion element on a swab stick:

| Ingredient | (Amount Parts by Weight) |
| --- | --- |
| Ethylene-vinyl acetate copolymer (ELVAX 40-W brand) | 100 |
| Hydroenated polyterpene resin (ARKON P-140 brand) | 50 |
| Rosin (SYLVATAC 80N brand) | 20 |
| Epoxidized soya oil (PLASTOFLEX 2307 brand) | 40 |
| Butyl benzyl phthalate (SANTICIZER 160 brand) | 28 |
| Diisodecylphthalate plasticizer (JAYFLEX brand) | 12 |
| Octyltin mercaptide stabilizer (IRGASTAB T-266 brand) | 3 |

EXAMPLE 11

Another, improved adhesion ethylene-vinyl acetate composition was used to form the cushion element on a swab stick:

| Ingredient | Amount (Parts by Weight) |
| --- | --- |
| Ethylene-vinyl acetate copolymer (ELVAX 40W brand) | 100 |
| Hydrogenatd polyterpene resin (ARKON P-140 brand) | 20 |
| Petroleum hydrocarbon (EASTOTAC 5H-100 brand) | 20 |
| Butyl benzyl phthalate (SANTICIZER 160 brand) | 30 |

EXAMPLE 12

Another ethylene-vinyl acetate copolymer formulation was prepared from:

| Ingredient | Amount (Parts by Weight) |
| --- | --- |
| Ethylene-vinyl acetate copolymer (ELVAX 40-W brand) | 100 |
| Petroleum hydrocarbon (EASTOTAC 5 H-100 brand) | 50 |
| Butyl rubber (KALENE brand) | 50 |
| Butyl benzyl phthalate (SANTICIZER 160 brand) | 50 |

The foregoing represents certain embodiments of the present invention, but should not be construed in a limiting sense. The scope of protection that is requested is set forth in the claims which follow.

We claim:

1. An improved applicator swab which comprises:
   (a) an applicator stick;
   (b) a resilient cushion element mounted on at least one end of the stick; and
   (c) a swab tip mounted over the cushion element; such that the cushion element is mounted on the stick to lie between the applicator stick and the swab tip.
2. A swab as claimed in claim 1 wherein the cushion element comprises an adhesive material.
3. A swab as claimed in claim 1 wherein the cushion element comprises a hot melt adhesive material.
4. A swab as claimed in claim 1 wherein the swab tip comprises cotton.
5. A swab as claimed in claim 2 wherein the swab tip comprises cotton.
6. A swab as claimed in claim 3 wherein the swab tip comprises cotton.
7. A swab as claimed in claim 1 wherein the applicator stick has two ends, each of which has a cushion element and swab tip thereon.
8. A swab as claimed in claim 7 wherein the cushion element comprises an adhesive material.
9. A swab as claimed in claim 7 wherein the cushion element comprises a hot melt adhesive material.
10. A swab as claimed in claim 7 wherein the swab tip comprises cotton.
11. A swab as claimed in claim 8 wherein the swab tip comprises cotton.
12. A swab as claimed in claim 9 wherein the swab tip comprises cotton.

* * * * *